United States Patent
Höglund

(10) Patent No.: US 6,427,692 B1
(45) Date of Patent: Aug. 6, 2002

(54) VALVE

(75) Inventor: Kasper Höglund, Rönninge (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/356,036

(22) Filed: Jul. 16, 1999

(30) Foreign Application Priority Data

Aug. 19, 1998 (SE) .............................. 9802761

(51) Int. Cl.$^7$ ............................. A61M 16/00
(52) U.S. Cl. .................. 128/205.24; 128/911; 604/246
(58) Field of Search ........................ 128/204.23, 204.18, 128/204.24, 204.25, 207.14, 205.24, 207.15, 207.16, 911, 912; 604/96.01, 99.02, 99.03, 99.04, 167.03, 103.01, 101.02, 101.04, 103.05, 164.09, 164.1, 99.01, 167.01, 246, 247, 256, 264, 537

(56) References Cited

U.S. PATENT DOCUMENTS

| | | | | |
|---|---|---|---|---|
| 3,542,020 A | * | 11/1970 | Bushman ................. | 128/145.8 |
| 4,180,066 A | * | 12/1979 | Milliken et al. ....... | 128/205.24 |
| 4,316,458 A | * | 2/1982 | Hammerton-Fraser . | 128/205.24 |
| 4,519,388 A | * | 5/1985 | Schwanbom et al. .. | 128/204.25 |
| 5,165,398 A | * | 11/1992 | Nird ...................... | 128/204.25 |
| 5,487,383 A | * | 1/1996 | Levinson ............... | 128/207.15 |
| 5,606,968 A | * | 3/1997 | Mang .................... | 128/207.14 |
| 5,711,296 A | * | 1/1998 | Kolobow ............... | 128/205.13 |
| 5,740,796 A | * | 4/1998 | Skog .................... | 128/204.23 |
| 6,050,972 A | * | 4/2000 | Zadno-Azizi et al. ......... | 604/97 |

* cited by examiner

Primary Examiner—John G. Weiss
Assistant Examiner—Mital Patel
(74) Attorney, Agent, or Firm—Schiff Hardin & Waite

(57) ABSTRACT

A valve, particularly suited for use with a patient ventilation system to regulate respiration gas flow to and from the lungs of a patient has a substantially parallel, co-axial, arrangement of inner and outer fluid flow passages for conducting gas through the valve to and from a common flow conduit connected to the patient's lungs, each passage having gas flowing therein in a different direction. A cuff is provided which is inflatable to control the flow of fluid through the valve. The cuff is disposed so as to be able to form a fluid-tight seal against one or other of the facing surfaces of the inner and the outer flow passages when inflated, and to block flow through the outer passage in a timed relationship with the breathing cycle of the patient.

8 Claims, 3 Drawing Sheets

VALVE

BACKGROUND OF THE INVENTION

1. Field of the Invention

The present invention relates to a valve and in particular to a valve of the type which is connectable to common flow path for inspiration and expiration gas in a patient ventilation system to provide separate the flows paths of the inspiration and expiration gases.

2. Description of the Prior Art

Known patient ventilation systems, such as respirators, ventilators and anaesthetic delivery systems, have associated tubing circuits. These tubing circuits commonly include an inspiration gas line for delivering breathing gas from the ventilation system to a patient and an expiration gas line for taking expired gas from the patient to the air or other expiration gas receiving facility. In common usage the tubing circuit may need to be frequently removed for cleaning or replacement, perhaps on a daily basis, in order to minimize the possibility of bacterial growth within the circuit which could infect the patient. Additionally, long lengths of flexible tubing in an inspiration branch and a,separate expiration branch make the determination of the patient's tidal volume and lung-thorax compliance difficult since the tubing tends to expand and contract radially in response to pressure variations during a breathing cycle. Patient comfort needs also to be considered and some patients, especially "home-care" patients, wish to move around in their "care environment", and obviously the smaller the amount of tubing the easier and more comfortable it will be for them as they move. It is therefore desirable to minimize the length and the number of tubes within the circuit.

This may be achieved by providing a common flow path for the inspiration and the expiration gases which therefore replaces two gas lines with only one for a part of the tubing circuit. In order to be able to do this, a valve arrangement is required that is able to separate inspiration and expiration gas flows in order to prevent the patient from re-breathing expired gases, or to enable the inspiration gas and the expiration gas to be treated separately within the ventilation system.

One known valve which is used in ventilation systems to achieve this result is disclosed in U.S. Pat. No. 5,002,050. This valve has a valve body with an inlet for inspiration gas, an outlet for expiration gas and a common inlet/outlet for connecting the valve to the airway of a patient. Concentrically arranged inner and outer gas flow conduits are also provided, each having one end connected to the common inlet/outlet via a common gas flow passage and opposite ends respectively connected to the inlet and the outlet. A differential area valving means is located towards the end of the inner conduit and is arranged so that inspiration gas always impinges on its larger surface area. This inspiration gas provides operational control of the valve so that its opening and closing is dependent on the pressure exerted by the inspiration gas on the valving means. The valving means is slidable along the common axis of the valve in response to the flow of pressurized inspiration gas through the valve to seal the end of the common gas flow passage and block gas communication between the valve outlet and the common passage. When the pressure exerted on the differential area valving means by the expiration gas exceeds that exerted by the inspiration gas, the valving means slides in the opposite direction to unblock the end of the common passage way and permit egress of expiration gas past the valving means, into the outer conduit and out of the valve through the outlet. Further check valves are attached to the differential area valving means which permit only a unidirectional flow through the valving means.

This arrangement, however, is mechanically complex and the seal itself is made over a relatively small area, which is the end of a pipe, so that small particles may prevent a proper seal being formed. Moreover, once fabricated, and the differential area of the valving means set, the operation of the valve is controllable mainly by varying the relative pressures of inspiration and expiration gas acting on the different areas. Thus, the operation of the valve is controlled basically by varying the amount of gas within the inspiration line of the tubing circuit. This line has a relatively large volume, compared with that of the valve, and this leads to a relatively slow response of the valve to inspiration gas changes.

A further known valve is disclosed in U.S. Pat. No. 5,538,002 which has a pair of concentric tubes arranged to form a narrow channel therebetween through which breathing gas is supplied to a patient. The inner tube is arranged to connect the respiratory system of the patient to the outside and an inflatable cuff is disposed within the inner channel to expand and seal against itself as breathing gas passes through the outer, narrow channel. A disadvantage with this self-sealing arrangement is that a relatively poor gas seal may be formed. This is because if the cuff is substantially fully expanded to form the seal then the region of contact between the two surfaces is small, and if the cuff is less expanded wrinkles may form in the contacting surfaces which can lead to a poor seal or to the surfaces being separable at low pressures.

SUMMARY OF THE INVENTION

It is an object of the present invention to provide a structurally simple valve, useable in patient ventilation systems, in which a relatively large sealing area can be provided and in which operation of the actual valving components occurs substantially independently of the relative pressures of the inspiration and expiration gases within the tubing circuit.

The above object is achieved in accordance with the principles of the present invention in a valve having a substantially parallel, concentric arrangement of an inner fluid flow passage and an outer fluid flow passage for respectively conducting fluid through the valve to and from a common flow conduit, in opposite directions in the respective passages, and a cuff which is inflatable to control the flow of fluid through the valve, the cuff being inflatable to form a fluid-tight seal against one or the other of the facing surfaces of the inner and outer flow passages, so as to block fluid flow through the outer passage.

Thus, by providing a valving element in the form of an inflatable cuff that seals between overlapping regions of the outer surface of an inner conduit and the inner surface of an outer conduit which are arranged to be substantially parallel to, and preferably co-axial with one another, a seal is formed across a large area of the external surface of the cuff. Additionally, by having the inside of the cuff connectable with an external pressurized fluid source then the opening and closing of the valve need not rely on either of the inspiration gas or the expiration gas. Moreover, the valve is of a relatively simple construction with the valving element having only one moving part i.e. the inflatable cuff.

Preferably the degree of inflation of the cuff is controllable to provide a variable area flow restriction which may serve, for example, as a Positive End Expiratory Pressure (PEEP) valve useable in a ventilation system to regulate the exhaled gas flow to keep the lungs at a positive pressure throughout the expiratory phase of a patient's breathing cycle. Such PEEP ventilator operating modes are well known in the art but are achieved here in a novel manner. Additionally or alternatively, the variable area flow restriction may be used in conjunction with a differential pressure flow meter so that the size of the inflated cuff is varied in order to maintain the linearity of the meter over a large dynamic flow range. The operating principles of variable area flow restriction flow meters are well known in the art and are described, for example in U.S. Pat. Nos. 4,938,077 and 4,006,634.

The cuff may be formed integrally with the valve, attached to one or other of the inner and the outer conduit so as to provide a unitary design. This may be achieved, for example, by locating the cuff on the outer surface of the inner passage so that it inflates to seal against the inner surface of the outer passage.

DESCRIPTION OF THE PREFERRED EMBODIMENTS

Figure 1:
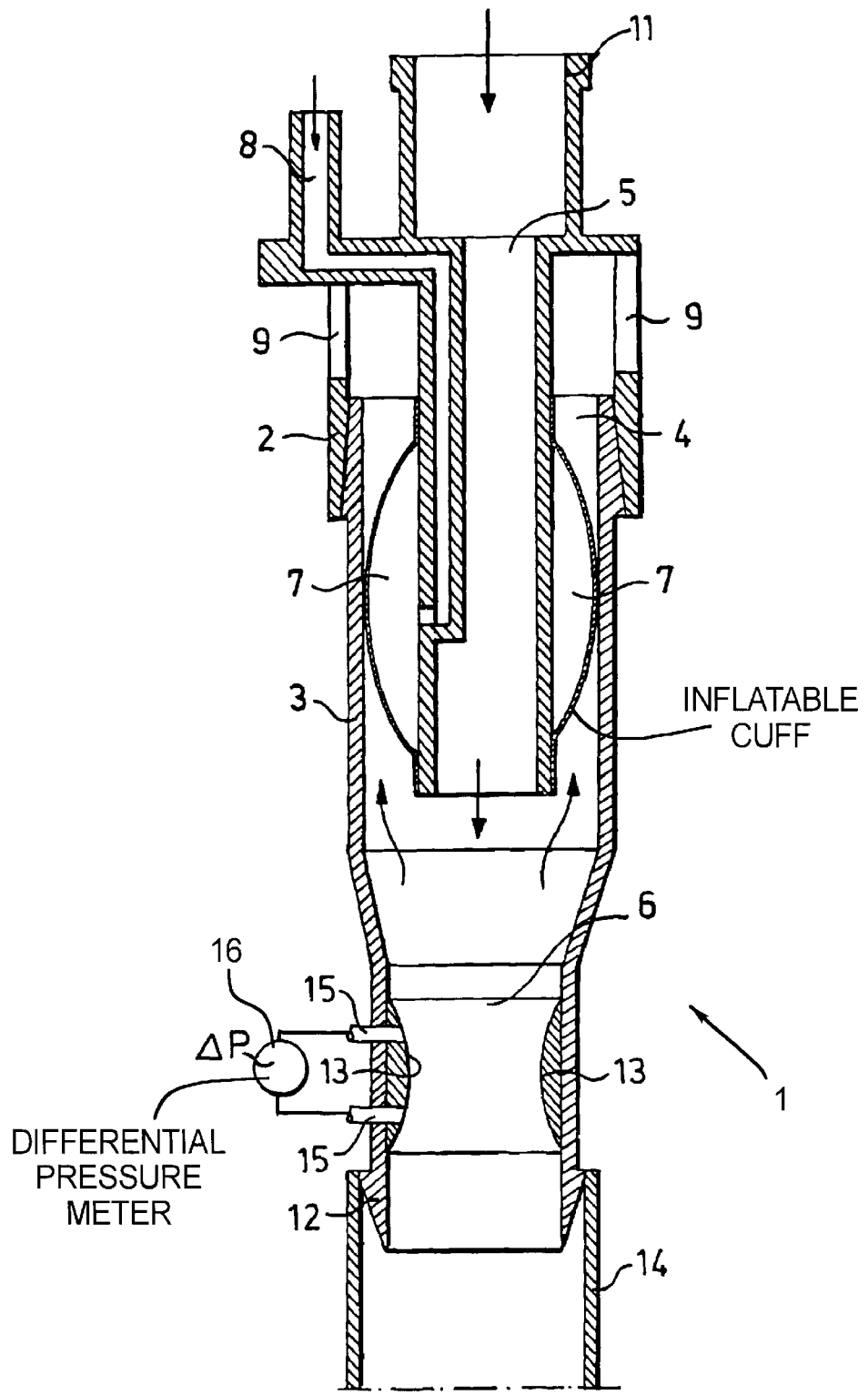
FIG. 1 is a sectional view of an embodiment of a valve constructed in accordance with the principles of the present invention.

As shown in FIG. 1, a valve 1 has, in this example, [two body sections 2,3] a first body section 2 and a second body section 3 which when interfitted, together form an outer fluid flow passage 4 and an inner fluid flow passage 5 co-axial therewith, and a common flow passage 6 through the valve 1. An inflatable cuff 7 is secured around its periphery to the external surface 40 of the inner flow passage 5, for example by using a suitable bonding agent. A further fluid passage 8 is a formed within the body section 2 and is connectable to a source of pressurized fluid (not shown) for inflating the cuff 7 to form a fluid tight seal against the inner surface 41 of the outer flow passage 4 block the outer flow passage 4, as illustrated in FIG. 1. A first connection piece 11 and a second connection piece 12 are formed on the first and second body sections 2 and 3 respectively, to facilitate the external connection of the valve 1 to fluid flow conduits (for example the tubing section 14 shown connected to the common flow passage 6).

The body section 2 is also provided with apertures 9 which, when the two body sections 2,3 are interfitted, are in fluid communication with the inner passage 4 of the valve 1. These apertures 9 thus provide for fluid communication external of the valve 1 and are co-operatively disposed with the cuff 7 so that, when expanded, the cuff 7 can block fluid flow to and from the apertures 9 to control fluid flow through the valve 1.

In the present example, a flow restriction 13 is located within the common flow passage 6 and flow channels 15 are provided in pressure communication with the common flow passage 6 either side of the flow restriction 13. These channels are connectable to a standard differential pressure flow meter 16 to provide flow measurements for fluid proceeding in both directions within the valve 1 i.e. into and out of the common flow passage 6.

As shown in FIG. 1, the valve 1 is configured with the connection piece 11 acting as an inlet for fluid flow through inner flow passage 5 and in to the common flow passage 6. The apertures 9 then act as outlets for fluid flowing from the common flow passage 6 and through the outer passage 4. Pressurized fluid flows through the fluid passage 8 to the cuff 7 to inflate it and seal the outer passage 4 when fluid flows through the valve 1 from the inner passage 5. To reverse the direction of flow through the valve 1 the cuff 7 is deflated by removing the pressurized fluid therefrom and fluid can flow from the common flow passage 6 to the apertures 9.

Figure 2:
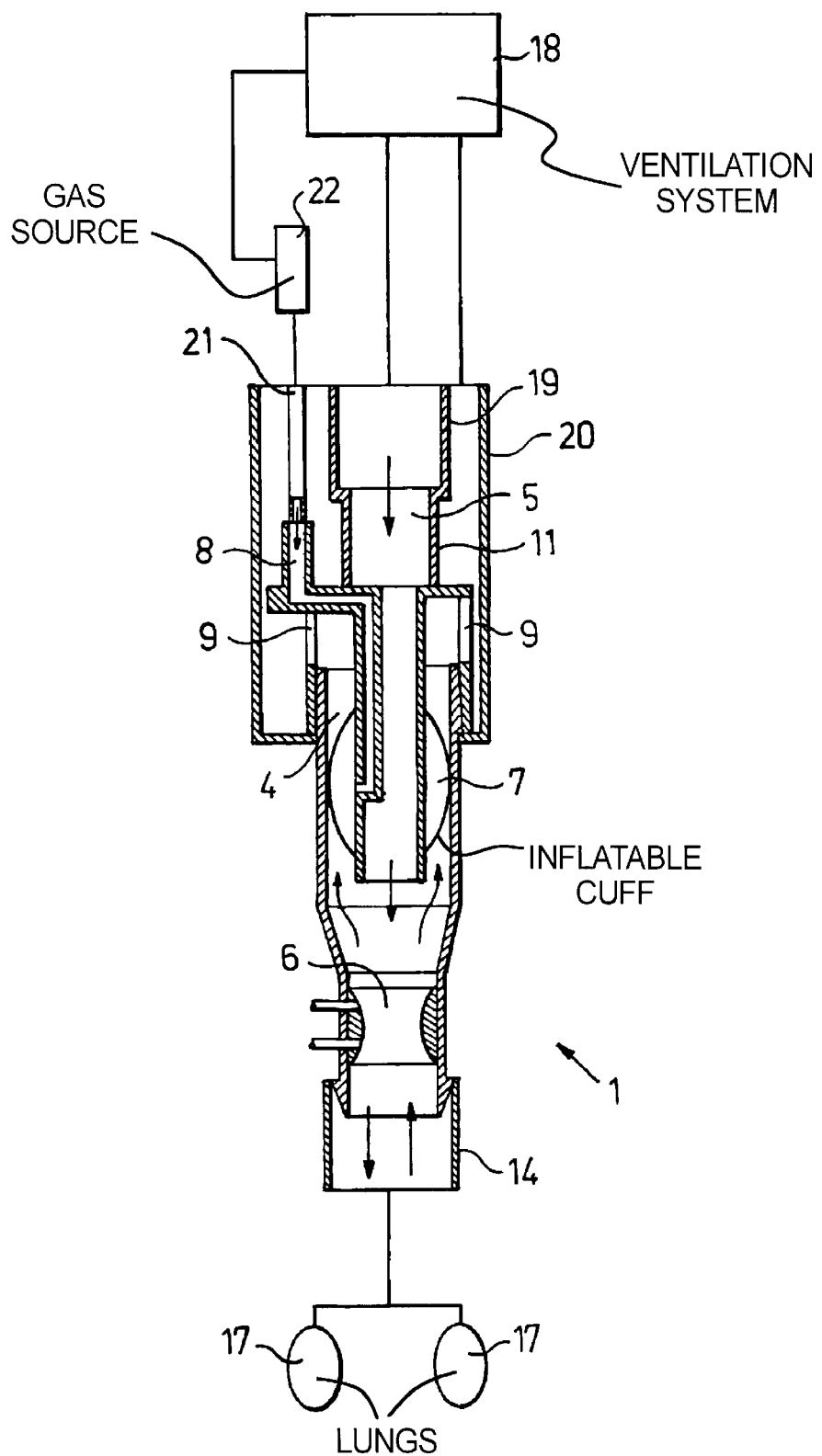
FIG. 2 shows a schematic representation of a tubing circuit of a patient ventilation system including the inventive valve.

As shown in FIG. 2, one use of the valve of the present invention, such as the embodiment shown in FIG. 1, is to control the flow of respiration gases (the flow directions of which are shown in FIG. 2 by the arrows) within a tubing circuit of a patient ventilation system, such as might include a ventilator or a respirator, as further described below.

The valve 1 is connected between connected between the lungs of a patient 17 and a known patient ventilation system 18 to control the flow of gas between the patient 17 and the ventilation system 18. An inspiration gas line 19 passes from the ventilation system 18 and seals in a gas tight connection to the connection piece 11 of the inner gas passage 5. An expiration gas line 20 passes from the ventilation system 18 and is connected in a gas tight seal with the body section 2 to enclose the outlet apertures 9. The inspiration line 19 and the expiration line 20 are configured concentrically for at least part of their lengths proximal the valve 1. A small bore lumen tubing 21 connects the cuff passage 8 with a pressurized gas source 22. This gas source 22 preferably contains or supplies a gas which is harmless to humans in order to minimize harm to the patient in case of its unexpected leakage into the valve 1. The gas source 22 is operatively inked to the ventilator system 18 so that supply of the pressurized gas to the cuff 7 can be timed with an operating cycle of the ventilation system 18, for example inflation of the cuff 7 may be triggered at the onset of the mechanical assisted inspiration phase of a patient's breathing cycle.

The common flow passage 6 of the valve 1 is connected in a gas-tight seal with a common flow conduit 14, which may be an inlet to a face mask (not shown) or an endotracheal tube, through which both inspiration gas to the lungs 17 and expiration gas from the lungs 17 alternately flow.

In use, the ventilation system 18 supplies a volume of inspiration gas as an output into the inspiration tubing 19 during an inspiration phase of the patient and also triggers the supply of pressurized gas from the source 22 to inflate the cuff 7 and block the outer passage 4 and prevent gas flow through the apertures 9. The volume of inspiration gas therefore passes through the valve 1 from the inlet connection 11, through the inner passage 5 and to the common gas flow conduit 14. From the conduit 14 the inspiration gas is delivered into the lungs 17. During an expiration phase of the patient's breathing cycle a valve arrangement (not shown) within the ventilation system 18 closes to prevent supply of inspiration gas to the inner passage 5. The gas within the cuff 7 is removed, to be vented to the atmosphere or recovered for re-use by the source 22, and the outer passage 4 is unblocked as the cuff 7 deflates. Expiration gas passing from the lungs 17 into the common flow passage 6 of the valve 1 can flow through the outer passage 4, through the apertures 9 and into the expiration gas line 20 from where it is recovered by the ventilation system 18. Thus the cuff 7 acts as a valving arrangement to block and unblock the outer passage 4 of the valve 1 as it respectively inflates and deflates during the breathing cycle of the patient. Additionally, or alternatively, by controlling the manner in which the cuff 7 is deflated a variable area flow restriction in the expiration gas path may be provided. This may be used to control the expiration pressure of the patient while the exhaled gas passes the partially deflated cuff 7 a nd so provides a PEEP mode of ventilation the therapy.

Figure 3:
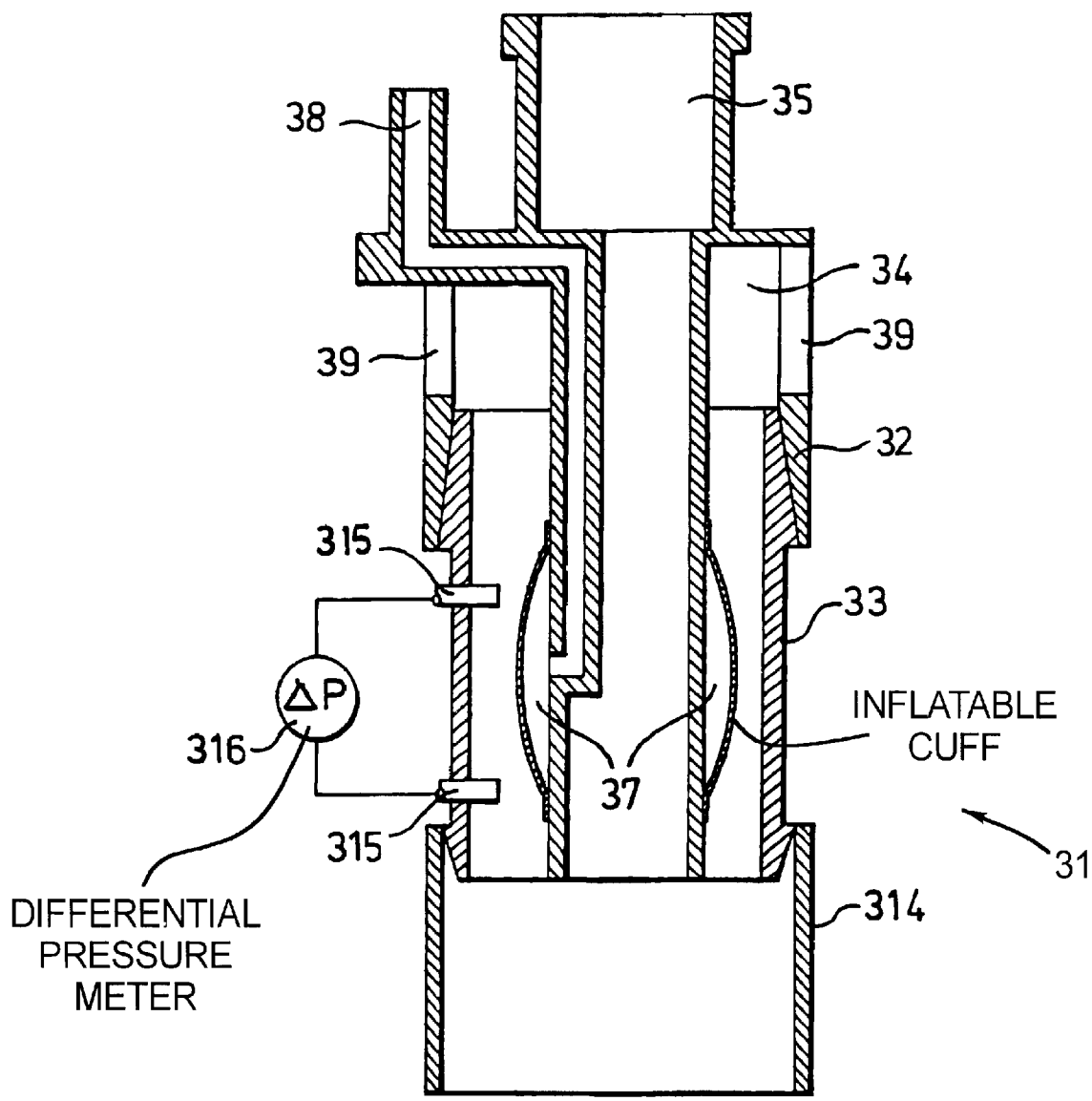
FIG. 3 shows an alternative embodiment of a valve constructed in accordance with the principles of the present invention.

FIG. 3 shows a further embodiment of the valve of the present invention. Similar to the valve of FIG. 1, the valve 31 has a first body section 32 and a second body section 33 which, when interfitted, form an inner fluid flow passage 35 and an outer fluid flow passage 34. The body portion 32 is provided with apertures 39 which in the assembled valve 31 provide fluid communication between the outer flow passage 34 and external of the valve 31. Different to FIG. 1 is that the first and second body sections 32 and 33 are of lengths such that no common flow passage is formed within the valve 31. Instead the body section 33 is connectable directly to a common flow passage 314. Sealed around the external surface 340 of the inner flow passage 35 is an inflatable cuff 37 which when inflated forms a fluid-tight seal against the inner surface 341 of the outer flow passage 34. The inflation and deflation of the cuff 37 is controlled by a pressurized gas source (not shown) which is connectable to the fluid passage 38. Ports 315 are provided in pressure communication with the outer flow passage 34, one either side of the cuff 37. A differential pressure flow meter 316 is connectable to the ports 315. The inflation of the cuff 7 is controlled to vary size the flow restriction it forms when partially inflated so as to provide a more linear response across the dynamic range of the meter 316.

It will be appreciated by those skilled in the art that the valves described above are examples of a valve according to the present invention. Modifications may be made to the valves described above while remaining within the scope of the invention. For example, the inner conduit may be adapted to carry the expiration gas and the outer the inspiration the inspiration gas; or the inflatable cuff may be fixedly located against the inner wall of the outer flow passage so as to seal against the outer wall of the inner flow passage when inflated; or the two part body may be formed as a single part, for example by using plastic injection molding techniques in its construction. Moreover, a one-way valve may be placed within the flow passage not to be sealed by the cuff to prevent a reverse flow through that passage instead of relying on existing valves normally present within the ventilation system, as are used in the above examples.

Although modifications and changes may be suggested by those skilled in the art, it is the intention of the inventor to embody within the patent warranted hereon all changes and modifications as reasonably and properly come within the scope of his contribution to the art.

I claim as my invention:

1. A valve, comprising:
an inner fluid flow passage;
an outer fluid flow passage surrounding and being substantially parallel to said inner fluid flow passage, said inner fluid flow passage and said outer fluid flow passage being connected to a common flow conduit and having fluid flow therein in respectively opposite directions relative to said common flow conduit, and said inner fluid flow passage having an outer surface and said outer fluid flow passage having an inner surface facing said outer surface; and
an inflatable cuff attached to one of said inner and outer surfaces and being inflatable to form a fluid-tight seal against the other of said inner and outer surfaces, to block flow of fluid through said outer fluid flow passage.

2. A valve as claimed in claim 1 wherein said cuff is inflatable to form said fluid-tight seal against the inner surface of said outer fluid flow passage.

3. A valve as claimed in claim 1 wherein said inner fluid flow passage has a length which is different from a length of said outer fluid flow passage, said length of said outer fluid flow passage extending beyond the length of said inner fluid flow passage to form a common flow passage, in communication with both said inner fluid flow passage and said outer fluid flow passage, connectable to said common flow conduit.

4. A valve as claimed in claim 1 further comprising a further fluid flow passage isolated from said inner fluid flow passage and said outer fluid flow passage, and disposed to conduct a pressurized fluid to and from an interior of said cuff from an external location to control inflation of said cuff.

5. A valve as claimed in claim 1 wherein said cuff is inflatable to provide a flow restriction having a variable area for fluid flow through said outer fluid flow passage.

6. A valve as claimed in claim 5 further comprising a differential pressure flow meter in communication with fluid flowing in said outer fluid flow passage at one side of said variable area flow restriction along a direction of flow, for measuring a pressure difference at said one side of said variable area flow restriction for identifying fluid flow through said outer fluid flow passage.

7. A ventilation tubing circuit comprising:
an inspiration gas line having a first end connectable to a source of inspiration gas;
an expiration gas line having a first end connectable with an expiration gas receiver;
a flow conduit, connected to said inspiration gas line and said expiration gas line and adapted for connection to an airway of a patient;
a valve comprising an inner fluid flow passage, an outer fluid flow passage surrounding and being substantially parallel to said inner fluid flow passage, said inner fluid flow passage and said outer fluid flow passage being connected to said flow conduit and having fluid flow therein in respectively opposite directions relative to said flow conduit, said inner fluid flow passage having an outer surface and said outer fluid flow passage having an inner surface facing said outer surface opposed, facing surfaces, and an inflatable cuff attached to one of said inner and outer surfaces which is inflatable to form a fluid-tight seal against the other of said inner and outer surfaces, to block flow of fluid through said outer fluid flow passage; and
said inner fluid flow passage of said valve being connected to a second end of one of said inspiration line and said expiration line, and said outer fluid flow passage of said valve being connected to a second end of the other of said inspiration line and said expiration line, to conduct respiration gases through said valve to and from said flow conduit.

8. A ventilation tubing circuit as claimed in claim 7 wherein said cuff is inflatable to provide a variable area flow restriction for fluid flow through said outer fluid flow passage, and means for controlling inflation of said cuff to provide a positive end expiratory pressure (PEEP).

* * * * *